United States Patent [19]

Shires

[11] Patent Number: 5,146,413

[45] Date of Patent: Sep. 8, 1992

[54] METHOD FOR THE DETERMINATE EVALUATION OF A CHEMISTRY ANALYZER'S COMBINED DILUTING AND ANALYZING SYSTEMS

[76] Inventor: Gary W. Shires, 124 E. Harvard Dr., Tempe, Ariz. 85283

[21] Appl. No.: 42,864

[22] Filed: Apr. 24, 1987

[51] Int. Cl.$^5$ .................................. G06F 15/20
[52] U.S. Cl. .............................. 364/497; 364/554; 73/1 H
[58] Field of Search ................... 73/1 H; 364/497, 554

[56] References Cited

U.S. PATENT DOCUMENTS 4,354,376 10/1988 Greenfield et al. ................. 73/1 H

OTHER PUBLICATIONS

Lambbeck; "Calibration of Small Volumetric Laboratory Glassware"; Institute For Basic Standards Dec. 19, 1974.

*Primary Examiner*—Parshotam S. Lall
*Assistant Examiner*—Ellis B. Ramirez

[57] ABSTRACT

A method for chemistry systems analysis to identify the performance of the functional components of the system, specifically, those of volumes dispensed and optical linearity. Employing a linear regression comparison between predetermined absorbance values, calculated from Beer's Law, and absorbance values obtained from the optical system under test, a value correction constant derived from the regression comparison may be applied to all subsequent absorbance values. Absorbance values, obtained from the optical system as a result of analyzing dilutions are by the pipetting system of material having a greater concentration but the same molar absorbtivity constant as the material used for the linearity evaluation, can be corrected to a value that does not reflect any optical system bias, and may be considered as the divident for the function of converting absorbance values into volumes dispensed. The divisor of the convertion function will be derived from the predetermined absorbance of the concentrate, using Beer's Law, and dividing that by the total volume requested by the volumes evaluation, leaving an absorbance value that equals a lul delivery. The volume dispensed by the pipetting system may then be calculated by dividing the corrected absorbance value by the lul absorbance value, yielding a quotient identifying the actual volume delivered.

1 Claim, No Drawings

METHOD FOR THE DETERMINATE EVALUATION OF A CHEMISTRY ANALYZER'S COMBINED DILUTING AND ANALYZING SYSTEMS

FIELD OF THE INVENTION

This process relates to chemistry analyzers and diluting systems and specifically to the accuracy and precision of each system.

DISCUSSION OF PRIOR ART

The determination of pipet volumes has been proposed by several methods, each has its inherent disadvantages.

A product manufactured by Quantimetrix called Voluquant TM is marketed as a pipet volume evaluation kit. Several disadvantages of this kit are apparent in the instructions of the kit. First, the instructions call for a calibration of the spectrophotometer and an assumption that the calibration is absolute and no bias exists in the spectrophotometer. Linearity of the optical system is assumed for the spectral line over the entire range of absorbance of the analyzer. No means for intercept or slope correlation of spectrophotometers results is provided. All volume determinations then reflect the bias of the chosen analytical instrument. Second, several manual dispensing processes accompany the procedural steps relying on individual laboratory technique and discounting any variance in this area of technique or support apparatus. Thirdly, a predetermined acceptance range is assigned for the absorbance data of the dilutions recovered from the evaluation by the spectrophotometer, again disregarding any instrument bias for a pass or fail determination. Pipettes can be misadjusted if this error is not indentified. Fourth, there is no method for producing an actual volume evaluation in the procedure. Means, standard deviation, and %CV are the only statistical evaluations provided. These are valid evaluations to do, however, they alone fall short in making a quatity judgment about the pipetting system by not providing a method to identify the actual volume dispensed. Fifth, there are no specific procedures for automated systems, leaving the task of generating a procedure up to the operator of that system. This reliance on operator development of a procedure leads to a more subjective method of evaluation based on operator skill and knowledge levels.

The volume calibration kit supplied by MLA has all the same disadvantages as the kit for Quantimetrix. The MLA kit does provide multiple point plotting of the optical response curve, however, no method of system bias removal is provided. Again volume valuations are subject to analytical errors.

Instrumentation Laboratories, Inc. developed a pipet precision test by doing an actual chemistry analysis and computing the results of the chemistry test for a %CV, and then assume pipet performance from this value. No actual volume dispensed can be calculated from the results. A separate linearity check is performed with different dilutions of NADH and PNP for the analyzer section of the chemistry system. The results of this test compare to some predetermined statistical values, however, no correlation of the pipetting system to the analytical system can be drawn from these tests as performed. The system as a whole is not evaluated with unity of purpose.

The Roche Company provides several methods for pipet and optical evaluations. These procedures come closest to giving a true picture of system performance, however, the same assumptions are made as in the Quantimetrix procedures about absorbance results and support apparatus used in the volume evaluations. An actual volume dispensed can be calculated if reference to a separate piece of equipment. The error here, of course, is how accurate is the separate piece of equipment? There is no mention of bias removal of the analitical devise used for this procedure.

OBJECTS OF THE INVENTION

It is an object of the present invention to provide a procedure and kit using chemical substances of known molar absorbtivity and mathmatical progressions which will allow pipetting and analytical evaluations of any given system configuration and reduce their results to the essence of origin.

It is also an object of the present invention to provide a procedure and kit using chemical substances of known molar absorbtivity and mathmatical progressions which will allow qualification of chemistry analyzing systems through the identification and definition of quality control materials, their results and reactant capabilities.

A further object of the present invention is to provide a procedure and kit using chemical substances and mathmatical progressions for a multitude of spectral line evaluations.

A still further object of the present invention is to establish, through the use of the procedure and kit, a chemistry system quality control procedure, using chemical substances of known molar absorbtivity and mathmatical progressions, that is superior to, and more descriptive than, presently accepted laboratory criteria.

These and other objects may be accomplished by the method hereinafter described. A chemical substance is chosen that is traceable to NBS for its purity and accuracy for molecular weight. The chemical substances will have a well documented molar absorbtivity. The chemical substance can be dissolved in a buffer of sufficient ph and possessing 0 obsorbance characteristics for the chosen chemical substance peek spectral line frequency, to maintain the characteristic absorbance qualities of the chosen chemical substance at any dilution selected using said buffer as the diluent, thus maintaining an absorbance stability over the range of current laboratory analytical instrumentation. The chosen chemical substance is prediluted in a buffer having the same characteristics as the buffer solution used to dissolve the chemical substance to form a plurality of solutions of different concentrations to be labeled sequentially $X1 \ldots Xn$, and each manually placed in a reading cuvette of the analytical system. Multiple absorbance readings are taken for the buffer used as the diluent and each level of the prediluted chromophore concentrations covering the range of the analyzer's absorbance limits and labeled $Y1 \ldots Yn$. A linear regression evaluation is performed comparing each of the measured absorbance values of the different levels of concentrations as measured on the analytical system, to the corresponding precalculated absorbance value that has been calculated for each prediluted level using Beer's Law, $A = abc$, where $A$ = absorbance of the chromophore, $a$ = the molar extinction coefficient of the chromophore, $b$ = the optical path length of the chromophore, and $c$ = the molar concentration of the chromophore.

For the linear regression comparison, the X1 . . . Xn values, called the independent variables, will be the calculated absorbance value for each level of prediluted chromophore and will be corrrespondingly compared to the Y1 . . . Yn values, called the dependent variables, which will be the mean measured absorbance value obtained for each prediluted chromophore minus the mean blank absorbance value obtained from the absorbance measurement of the buffer used as the diluent.

The linear regression results identifies the optical system characteristics using the slope, intercept, coefficient of correlation, and root mean squared deviation. This information can now be used to mathmatically correct the optical system and view the subsequent absorbances in a more objective manner.

A solution of a more concentrated form of the same chemical substance used in the analytical evaluation is then placed in reservoirs on the system where samples are normally drawn from and will be aspirated by the system's sample pipet from those reservoirs. Buffer used for the original formation of the chromophore concentrate is placed in the reservoirs where reagents are normally drawn from, and will be aspirated by the systems reagent pipet from those reservoirs. The chromophore concentrate aspirated by the sample pipet from an individual sample reservoir is then delivered to an individual cuvette along with the buffer that was aspirated by the reagent pipet from the reagent reservoir. These two volume then become the total volume in the individual measuring cuvette. The process of delivering a single sample volume and a single reagent volume to each individual measuring cuvette can be repeated for precision analysis of chromophore and buffer volume combinations. The total volume in each individual measuring cuvette is then analyzed for absorbance by the analytical system. The level of absorbance will depend on the chromophore and buffer combination. Since the buffer is optically clear at the chromophore peak absorbance spectral line frequency, the accomplishment of accurate chromophore and buffer delivery into the measuring cuvette will be reflected by obtaining a plurality of absorbance readings for each individual measuring cuvette and finding a mean measured absorbance value from those absorbance readings and subtracting the means buffer blank absorbance from the mean measured absorbance of the individual measuring cuvette. Mathmatically correct that absorbance value for analytical system bias by subtracting the intercept value from the lear regression comparison and dividing that result by the slope value from the linear regression comparison. This corrected absorbance value can now be divided by a unit absorbance value that will be calculated using Beer's Law to establish the absorbance for the chromophore concentration and dividing that absorbance by the total volume of both sample and reagent volumes delivered to the measuring cuvette. Since the success of a reaction chemistry depends on the sample to reagent ratio, the ability of the pipetting system to deliver the requested amount of chromophore and buffer will be calculated by the corrected measured absorbance divided by a unit absorbance yielding a value of chromophore delivered to the measuring cuvette that has been diluted by the buffer delivered to the same measuring cuvette. For example: if the chromophore concentrate of 10 and the buffer has an absorbance value of 0, a sample to reagent ratio of 3 parts sample to 197 parts reagent would be checked by programming the system sample and reagent delivery pipets to aspirate and deliver to a measuring cuvette 3 microliters of chromophore as a sample and 197 microliters of buffer as reagent. The chromophore concentrate absorbance of 10 is divided by the total volume of 200 microliters of sample and reagent yielding and unit absorbance value of 0.05 absorbance units per microliter of total volume in the measuring cuvette. If the corrected absorbance value equaled 0.15 absorbance units, then, 0.15 divided by 0.05 would equal 3 which is the microliter volume of sample requested. The remainder of the total volume in the measuring cuvette would be 197 microliters of buffer since the buffer does not absorb light and has an absorbance value of 0 and thereby acts as a diluting medium. If the sample volume were greatly in error from the manufacturers specifications, then this would indicate an error in the sample and or reagent volumes and further tests would be necessary to identify the pipet system in error. This can be accomplished by altering the sample volume while maintaining the same reagent volume.

The errors for sample and reagent pipetting and absorbance analysis can thereby be separated and defined. The chemistry system itself can be evaluated for the integrity of each process step of the system. Pipetting and absorbance analysis can be evaluated separate from running an actual chemistry, which involves materials whose performance variables cannot be controlled by the operator, such as reagents, controls, and calibrators.

Once the performance characteristics of a chemistry analysis system are properly identified and tracked through repeated evaluations, a confidence level is generated for that system.

The absorbant data of each reactant product through the progression of the analysis now becomes very characteristic of the stepwise reactions of the multiple reactants involved in a chemistry analysis. Quality control for each step can be established. The establishment of such a quality control method builds into the system a means by which repeatable performance characteristics for each step of the reaction can be defined for any chemistry procedure applied to that system. Troubleshooting of chemistry result anomalies can be economically and specifically resolved, preventing expensive multiple replicate procedures where no known cause can be otherwise identified, which would direct the operator to the proper corrective action.

The invention will become even more apparent from the following detailed description with references to the scientific and mathmatical principles involved.

DESCRIPTION OF THE INVENTION

The molar absorbtivity of a specific chemical substance is based on its molecular weight, which is calculable from the Periodic Table of Elements, the concentration of the absorbant, and the pathlength at which it is analyzed. The absorbance will be quite specific for a given spectral line and will supported by Beer's Law, which states:

$$A = abc \tag{1}$$

Where:
A = absorbance
a = molar absorbtivity
b = pathlength
c = molar concentration Beer's Law is the basis for all absorbance evaluations and is the prime design criteria for current commercial instrumentation, and therefore becomes a common denominator for all analytical instruments employing absorbance or transmittance as the analytical method. This is the basis for all further calculations of the kit results.

The linear regression procedure employed to compare a plurality of measured absorbances of a plurality of different prediluted chemical substances of known molar absorbtivity and concentration to a plurality of corresponding absorbance values calculated using Beer's Law for the chemical substance and the corresponding predilution level of the chemical substance is a least squares analysis yielding informaton about the comparison of each corresponding measured absorbance and precalculated absorbance in the form of a slope, intercept, coefficient of correlation, and a root mean squared deviation, also known as standard error of estimate.

The formula for correcting the plurality of measured absorbances to produce a single absorbance value for each prediluted level of chromophore that reflects the analytical conditions of a system having no analytical bias altering those measured absorbances and can be viewed as responding only to Beer's Law for that formulated chromophore is:

Equation 5:

Mean measured absorbance minus mean measured blank absorbance of buffer diluent minus the intercept divided by the slope equals the corrected absorbance.

This formula is accepted by the National Committee for Clinical Laboratory Standards as one that is designed to identify determinent differences in results of simular analyses.

The formulae describing the least squares analysis comparison line are:

$$Y = a_0 + a_1 X \qquad (2)$$

Y = Any of the mean measured absorbance values of the prediluted chromophore.
X = The corresponding prediluted calculated absorbance value to that which was measured and chosen for Y.
$a_0$ = intercept
$a_1$ = slope The formula used to compute the coefficient of correlation is:

$$r^2 \pm \sqrt{\frac{\Sigma(Y\,est. - \overline{Y})^2}{\Sigma(Y - \overline{Y})^2}} \qquad \text{Equation 3}$$

Y est = any predicted value of mean measured absorbance for the chromophore.
$\overline{Y}$ = average of all mean measured absorbance values of the plurality of prediluted chromophore.
Y = mean measured absorbance value for each prediluted chromophore.
The term $\Sigma(Y\,est - \overline{Y})^2 = ((Y\,esti - \overline{Y}) + (Y\,est2 - \overline{Y}) + \ldots (Y\,estn - \overline{Y}))^2$
The term $\Sigma(Y - \overline{Y})^2 = ((Y1 - \overline{Y}) + (Y2 - \overline{Y}) + \ldots (Yn - \overline{Y}))^2$ The formula used to compute root means squared deviation or standard error of estimate is:

$$Sy.x \sqrt{\frac{\Sigma Y^2 - a_0 \Sigma Y - a_1 \Sigma XY}{N - 2}} \qquad \text{Equation 4}$$

Y = the mean measured absorbance value for each prediluted level of chromophore.
X = the calculated absorbance value for each prediluted chromophore.
$a_0$ = intercept
$a_1$ = slope
N = number of xy data pairs
The term $\Sigma Y^a = ((Y1 + Y2 \ldots Yn))^2$
The term $\Sigma Y = (Y1 = Y2 \ldots Yn)$
The term $\Sigma XY = (X1Y1) + (X2Y2) \ldots + (XnYn)$ The corrected absorbance is divided by a unit absorbance value for the total volume analyzed in the measuring cuvette which is calculated using Beer's Law for the chosen chromophore and the total volume of chromophore concentrate plus buffer diluent delivered to the measuring cuvette. An example is:

Equation 6:

The calculated absorbance of the chromophore concentrate divided by the total volume dilution (chromophore concentrate plus buffer) equals the unit absorbance value for the total volume of the chromophore concentrate plus buffer contained in the measuring cuvette (Absorbance value per microliter of total volume contained in the measuring cuvette).

The dispensed sample volume is now calculated using:

Equation 7:

$$\frac{\text{corrected measured absorbance}}{\text{unit absorbance value}} = \text{sample volume dispensed}$$

The buffer volume dispensed is the difference between the total volume delivered to the measuring cuvette minus the sample volume dispensed from equation 7.

Standard statistical computations for mean sample pipet volume, standard deviation, and %CV are employed to define the cumulative replicate evaluations. To identify, they are:

$$Y = \frac{\Sigma Y}{n} \qquad \text{Equation 8}$$

Y = mean sample volume dispensed $$SD = \sqrt{\frac{\Sigma Y^2 - \frac{(\Sigma Y)^2}{n}}{n - 1}} \qquad \text{Equation 9}$$

n = number of times the evaluation was done $\Sigma Y$ = sum of all sample volumes dispensed ($Y1 \ldots Yn$)

$$\% CV = \left(\frac{SD}{Y}\right) 100 \qquad \text{Equation 10}$$

OPERATION OF THE INVENTION

A plurality of different levels of prediluted chromophore concentrations covering the absorbance of the analyzer and buffer diluent from the kit are placed manually into individual reading cuvettes of the analytical system under evaluation and are analyzed for a plurality of absorbance readings for each prediluted chromophore and a buffer blank absorbance for the buffer diluent. The Beer's Law formula is used to arrive at a calculated (Equation 1).

The plurality measured absorbance for each prediluted chromophore and the buffer diluant are each averaged to produce a means absorbance value for each level of prediluted chromophore and a mean blank absorbance for the buffer diluent.

The mean measured absorbance values for each level of prediluted chromophore minus the mean buffer blank absorbance value are compared to the corresponding precalculated absorbance values, of each level of prediluted chromophore using the linear regression comparison method as determined by (Equation 2), where the mean measured absorbance values minus the mean blank absorbance of the buffer diluent are the Y1 ... Yn values and the calculated absorbance values for each level of prediluted chromophore are the corresponding X1 ... Xn values. A coefficient of correlation is calculated. (Equation 3). A root mean squared deviation, also known as standard error or estimate is optionally calculated (Equation 4). These calculations are standard and usually contained in laboratory computer software or mini calculators.

Having satisfactorily met the criteria for the scope of the statistical exercises which is set by the user of the kit, one proceeds with the placement of the chromophore concentrate contained in the kit, in a sample reservoir from which the chromophore concentrate will be aspirated by the system's sample pipet and delivered to the measuring cuvette. Buffer diluent is placed into the reagent reservoir from which the buffer diluent will be aspirated by the system's reagent pipet and delivered to the measuring cuvette to combine with the chromophore concentrate delivered by the system sample pipet. Analysis for the absorbance of the combination of one sample volume of chromophore concentrate plus one reagent volume of buffer diluent will produce a plurality of measured absorbance values for that individual measuring cuvette.

These values, $Y_1' \ldots Y_n''$, are then averaged and a mean value, $\overline{Y}'$ for each combination of chromophore concentrate and buffer diluent is established. Each measured mean absorbance value is then corrected for optical system bias. (Equation 5). This will be done for each measuring cuvette containing a combination of chromophore concentrate as delivered by the sample pipet plus buffer diluent as delivered by the reagent pipet.

The unit absorbance value for the chromophore concentrate is arrived at using Beer's Law, Equation 1, and dividing that chromophore concentrate absorbance value by the total volume of chromophore concentration plus buffer diluent delivered to the measuring cuvette. This unit absorbance value is arrived at through the mathmatical progression illustrated in Equation 6. This step, however, is performed for the user by the manufacturer of the kit, and the value will be contained in the instructions of each kit. This is done for the user because the chromophore concentrate provided in each kit will be dependent on the type of chemistry system under evaluation. The concentrate itself is substance and total volume dependant.

The corrected observed absorbance value, Equation 5, is then divided by the unit absorbance value, Equation 6, to obtain a volume dispensed value. (Equation 7).

Replicate volumes can be tested for precision by using the process in Equations 8, 9, and 10.

All results are to be recorded and continually updated with each evaluation performed.

These scientific principles and mathmatical progressions applied in this specific manner allow the evaluation of a chemistry analyzer system to be impartial and quite descriptive.

While the above description contains many specificities, these should not be construed as limitations on the scope of the invention, but rather as an exemplification of one perferred embodiment thereof.

Many other variations are possible, for example: separate pipetting systems can be evaluated on a single analyzer, several analyzers can be evaluated using a single pipetting system, or the kit contents can be split to analyze only one element of a chemistry system. Accordingly, the scope of the invention should be determined not by the embodiment illustrated, but by the intended claims and their legal equivalent.

I claim:

1. A method for determining the actual volume of a liquid dispensed from a liquid dispensing system through a sequence of evaluations whereby first, (i), a spectrophotometer is evaluated through the absorbance analysis of at least five different concentrations of a liquid chromophore, whose absorbance values will be calculated to fall within the absorbance detection limits for the spectrophotometer through the application of Beer's Law for the chromophore, (A=abc, where A=absorbance, a=molar extinction coefficient, b=sample pathlength, and c=molar concentration), and will be used in step two, (2), as the X values in the plot of a linear regression comparison curve, which is accomplished by using least squares analysis of X and Y data pairs expressing a line described by the equation Y=ao+a1X, (where ao=intercept $$a0 = \frac{(\Sigma Y)(\Sigma X^2) - (\Sigma X)(\Sigma XY)}{N\Sigma X^2 - (\Sigma X)^2}$$

and a1=slope), $$a1 = \frac{N\Sigma XY - (\Sigma X)(\Sigma Y)}{N\Sigma X^2 - (\Sigma X)^2}$$

and comparing to the Y values of the linear regression comparison that are the absorbance values obtained from the spectrophotometer absorbance analysis of each of the five known liquid chromophore concentrations, and producing a linear relationship of the known absorbance values of the five liquid chromophores to the absorbance values of the five liquid chromophore assays from the spectrophotometer that will be characterized by linear regression curve constants of slope, intercept, coefficient of correlation:

$$r^2 = +/- \sqrt{\frac{\Sigma(Y\,est. - Y)^2}{\Sigma(Y - Y)^2}}$$

and standard error of estimate:

$$Sy.x \sqrt{\frac{\Sigma Y^2 - a_0 \Sigma Y - a_1 \Sigma XY}{N-2}}$$

of which the slope and intercept constants will be used to adjust the spectrophotometer absorbance values obtained for use in step four (4), r will describe the one to the one relationship of the X and Y data pairs, and Sy.x will describe the proximity of the X and Y data points to the regression line, where in step three (3), a liquid chromophore of the same molecular type used to evaluate the spectrophotometer in steps one (1) and two (2), but of increased known concentration and whose absorbance value is calculated through application of Beer's Law, as in step one (1), (identified as AULC-absorbance of undiluted liquid chromophore), is diluted by the liquid dispensing system producing a solution of diluted liquid chromophore to be place into the spectrophotometer, previously characterized through linear regression by the five levels of known liquid chromophore absorbance values, and analyzed for the absorbance of the diluted liquid chromophore, (identified by the symbol ADLC), where in step four (4), the intercept obtained from the linear regression comparison in step two (2) will be subtracted from the absorbance value of the diluted liquid chromophore obtained in step three (3), (identified by the symbol ADLCi), (ADLC-ao=ADLC1), where in step five (5), the absorbance result from step four (4) will be divided by the slope value obtained from step two (2): (identified by the symbol ADLC2), (ACLC1/si=ADLC2), producing an absorbance value of the diluted liquid chromophore, as analyzed in step three (3) that has been adjusted by the linear regression constants of the spectrophotometer found in step two (2) to reflect the absorbance of the diluted liquid chromophore, as diluted by the dispensing system in step three (3), without absorbance response bias from the spectrophotometer used in step three (3), where in step six (6), a calculated total volume dilution absorbance value of the undiluted liquid chromophore, used in step three (3), (identified by the symbol TVDA), will be computed by dividing the known absorbance of the undiluted liquid chromophore used in step three (3), (identified by the symbol AULC), by the total volume of the dilution requested in step three (3), (identified by the symbol TV), (AULC/TV=TVDA), where in step seven (7), the adjusted absorbance value of the diluted liquid chromophore found in step five (5) will be divided by the calculated total volume dilution absorbance of the undiluted liquid chromophore found in step six (6), producing a result that represents the volume of undiluted liquid chromophore delivered for dilution in step three (3) by the dispensing system in volume units, (ADLC2/TVDA=Volume units delivered).

* * * * *